(12) United States Patent
Kaneko et al.

(10) Patent No.: US 11,793,901 B2
(45) Date of Patent: Oct. 24, 2023

(54) PASS BOX

(71) Applicant: Hitachi Industrial Equipment Systems Co., Ltd., Tokyo (JP)

(72) Inventors: Takeshi Kaneko, Tainai (JP); Takeshi Matsumura, Tainai (JP)

(73) Assignee: Hitachi Industrial Equipment Systems Co., Ltd., Tokyo (JP)

( * ) Notice: Subject to any disclaimer, the term of this patent is extended or adjusted under 35 U.S.C. 154(b) by 573 days.

(21) Appl. No.: 16/972,382

(22) PCT Filed: Jun. 10, 2020

(86) PCT No.: PCT/JP2020/022796
§ 371 (c)(1),
(2) Date: Dec. 4, 2020

(87) PCT Pub. No.: WO2021/250806
PCT Pub. Date: Dec. 16, 2021

(65) Prior Publication Data
US 2022/0184261 A1 Jun. 16, 2022

(51) Int. Cl.
*A61L 2/26* (2006.01)
*F24F 3/167* (2021.01)
*F24F 7/06* (2006.01)

(52) U.S. Cl.
CPC ............... *A61L 2/26* (2013.01); *F24F 3/167* (2021.01); *F24F 7/06* (2013.01); *A61L 2202/122* (2013.01); *A61L 2202/123* (2013.01)

(58) Field of Classification Search
CPC . A61L 2/26; A61L 2202/122; A61L 2202/123
See application file for complete search history.

(56) References Cited

U.S. PATENT DOCUMENTS

| 2010/0189607 A1* | 7/2010 | Yokoi | A61L 9/00 422/600 |
| 2015/0185121 A1* | 7/2015 | Kobayashi | A61L 9/00 422/547 |
| 2020/0121818 A1 | 4/2020 | Kaneko | |

FOREIGN PATENT DOCUMENTS

| JP | 1-239329 A | 9/1989 |
| JP | 1-288342 A | 11/1989 |
| JP | 4722642 B2 | 7/2011 |

(Continued)

OTHER PUBLICATIONS

International Search Report (PCT/ISA/220 & PCT/ISA/210) issued in PCT Application No. PCT/JP2020/022796 dated Sep. 1, 2020 (six (6) pages).

(Continued)

*Primary Examiner* — Sean E Conley
(74) *Attorney, Agent, or Firm* — Crowell & Moring LLP

(57) ABSTRACT

The present invention provides a pass box with which not only surface sterilization by means of a germicidal lamp on an article delivered in the pass box but also isolation of different articles can be performed in a space-saving manner, the cleanliness in the pass box is maintained, and mutual contamination is prevented during article delivery in the pass box. Air is sent from a blower of an upper pass box to an upper space of the upper pass box through a filter, the air is supplied to a lower space of a lower pass box via the upper space, and an airflow circulation path is provided to return the air that has passed through the lower space to the upper blower.

8 Claims, 6 Drawing Sheets

(56) References Cited

FOREIGN PATENT DOCUMENTS

| | | |
|---|---|---|
| JP | 2018-44748 A | 3/2018 |
| JP | 2018-114202 A | 7/2018 |
| WO | WO 2019/207894 A1 | 10/2019 |

OTHER PUBLICATIONS

Japanese-language Written Opinion (PCT/ISA/237) issued in PCT Application No. PCT/JP2020/022796 dated Sep. 1, 2020 (four (4) pages).

* cited by examiner

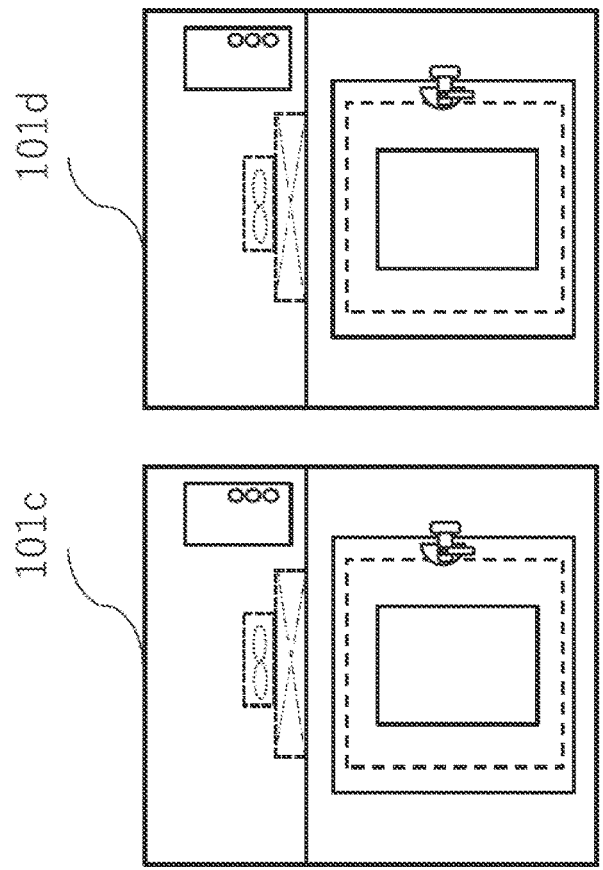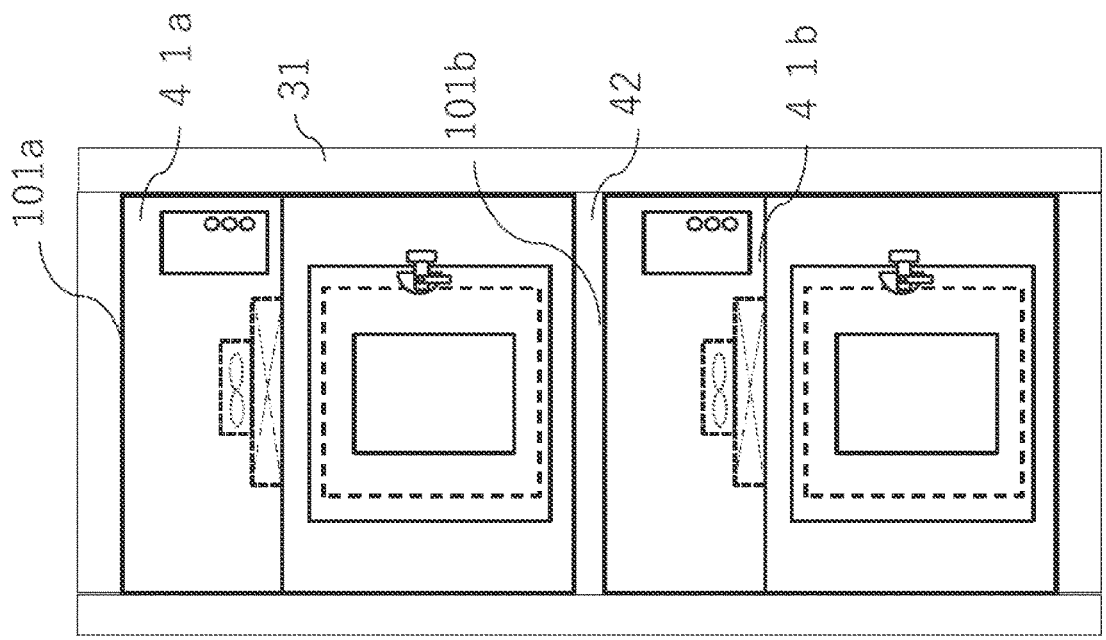

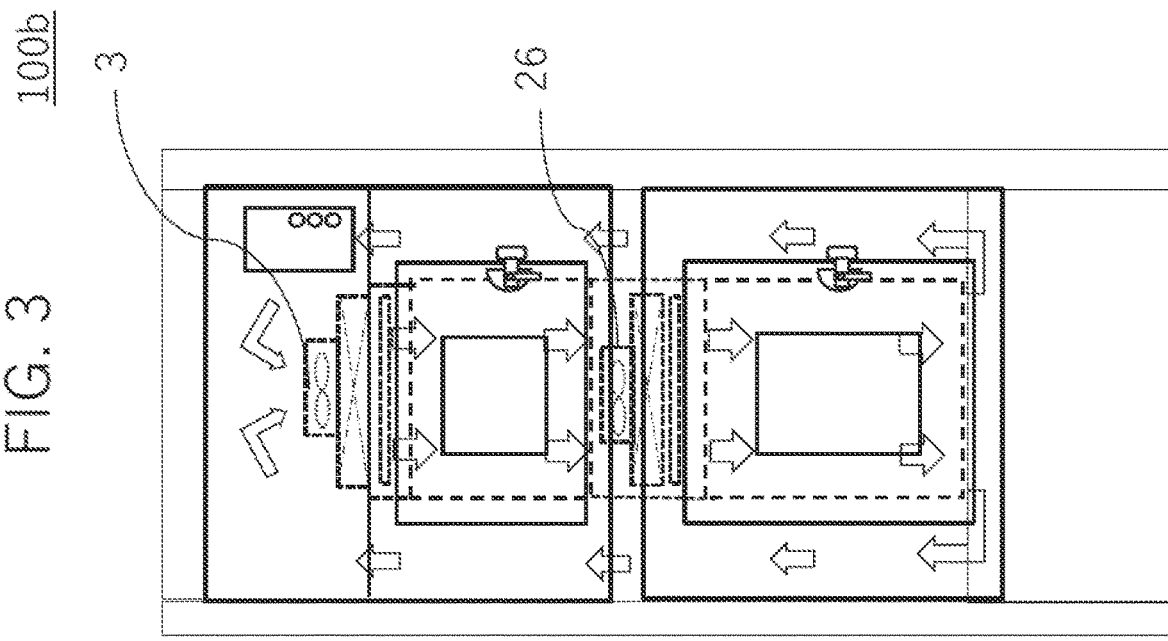

PASS BOX

TECHNICAL FIELD

The present invention relates to a pass box for taking a small article, sample, or the like in and out in the field of regenerative medicine where cells are cultured.

BACKGROUND ART

A person or a large article is taken in and out after removal of adhering dust or bacteria by means of an air shower so that the cleanliness of a clean room is maintained and dust or bacterial infiltration from the outside is prevented. A small article, sample, or the like is taken in and out with respect to a clean room by means of a pass box. The pass box for material delivery is used in industrial fields such as medical and pharmaceutical where pathogen handling and genetic manipulation are performed and is installed in a penetrating manner between rooms different in cleanliness from each other so that the cleanliness of the clean room is maintained.

Dirt or adhering dust is removed, by cleaning by means of alcohol or the like, before an article is put into the pass box. In addition, a germicidal lamp may be used so that the surface of what is handled is sterilized with the article put in by a pass box door being opened and the door being closed again.

Patent Document 1 illustrates an example of a pass box using a germicidal lamp.

CITATION LIST

Patent Document

Patent Document 1: JP 4722642 B2

SUMMARY OF THE INVENTION

Problems to be Solved by the Invention

In the field of regenerative medicine where cells are cultured, different articles such as equipment used for cell culture are delivered by means of a pass box for the purpose of mutual contamination prevention. The risk of contamination can be suppressed by the cleanliness in the pass box being ensured.

Although Patent Document 1 describes surface sterilization means based on ultraviolet irradiation by means of a germicidal lamp, Patent Document 1 does not consider the prevention of intra-pass box contamination attributable to dust generation caused by pass box door handle operation and dust leakage into a clean room that arise when an article is put in by means of the pass box.

In addition, Patent Document 1 does not consider pass box height suppression and workability improvement for the article that is put in and taken out.

An object of the present invention is to provide a pass box with which isolation of different articles can be performed in a space-saving manner, the cleanliness in the pass box is maintained, and mutual contamination is prevented during article delivery.

Solutions to Problems

In order to achieve the above object, an example of the "pass box" of the present invention, which is a pass box delivering an article with respect to a clean room, includes an upper pass box and a lower pass box, in which the upper pass box includes an upper blower provided in an upper portion, an upper HEPA filter provided downstream of the upper blower, a first door provided on the clean room side, a second door provided on a contaminated area side on a side opposite to the clean room, and an upper storage stand forming an upper space performing article delivery together with the first door, the second door, and the upper HEPA filter, the lower pass box is provided below the upper pass box and includes a lower HEPA filter provided downstream of the upper space, a third door provided on the clean room side, a fourth door provided on the contaminated area side on the side opposite to the clean room, and a lower storage stand forming a lower space performing article delivery together with the third door, the fourth door, and the lower HEPA filter, the upper blower sends air to the upper space, the air is supplied to the lower space via the upper space, and the pass box further has an airflow circulation path returning the air that has passed through the lower space to the upper blower.

In addition, another example of the "pass box" of the present invention, which is a pass box delivering an article with respect to a clean room, includes an upper pass box and a lower pass box, in which the upper pass box includes an upper blower provided in an upper portion, an upper HEPA filter provided downstream of the upper blower, a first door provided on the clean room side, a second door provided on a contaminated area side on a side opposite to the clean room, and an upper storage stand forming an upper space performing article delivery together with the first door, the second door, and the upper HEPA filter, the lower pass box is provided below the upper pass box and includes a third door provided on the clean room side, a fourth door provided on the contaminated area side on the side opposite to the clean room, and a lower storage stand forming a lower space performing article delivery together with the third door and the fourth door, an upper exhaust path allows air to flow toward a side wall of the upper pass box after the air passes through the upper space, a first airflow circulation path is formed between the side wall of the upper pass box and an upper space side wall forming the upper space to return air to the upper blower after the air passes through the upper space and the upper exhaust path from the upper blower, and an upper bypass path bypassing the upper space from the upper blower and sending air into the lower space and a second airflow circulation path returning the air to the upper blower between a side wall of the pass box and a lower space side wall forming the lower space are formed.

Effects of the Invention

According to the present invention, it is possible to prevent inter-article mutual contamination by delivering different articles in isolated spaces. In addition, it is possible to ensure the cleanliness of each article delivery space. In addition, the height of the pass box can be suppressed by the storage spaces being disposed in two (upper and lower) stages and it is possible to provide a pass box with improved workability for putting in and taking out articles.

Objects, configurations, and effects other than those described above will be clarified by the following description of an embodiment.

BRIEF DESCRIPTION OF THE DRAWINGS

FIG. 2A is a diagram illustrating a comparative example in which two pass boxes are disposed above and below.

FIG. 2B is a diagram illustrating a comparative example in which two pass boxes are disposed side by side.

FIG. 3 is a diagram illustrating an example of a two-stage (upper- and lower-stage) pass box (with a lower blower) of Example 2.

MODE FOR CARRYING OUT THE INVENTION

Figure 1A:
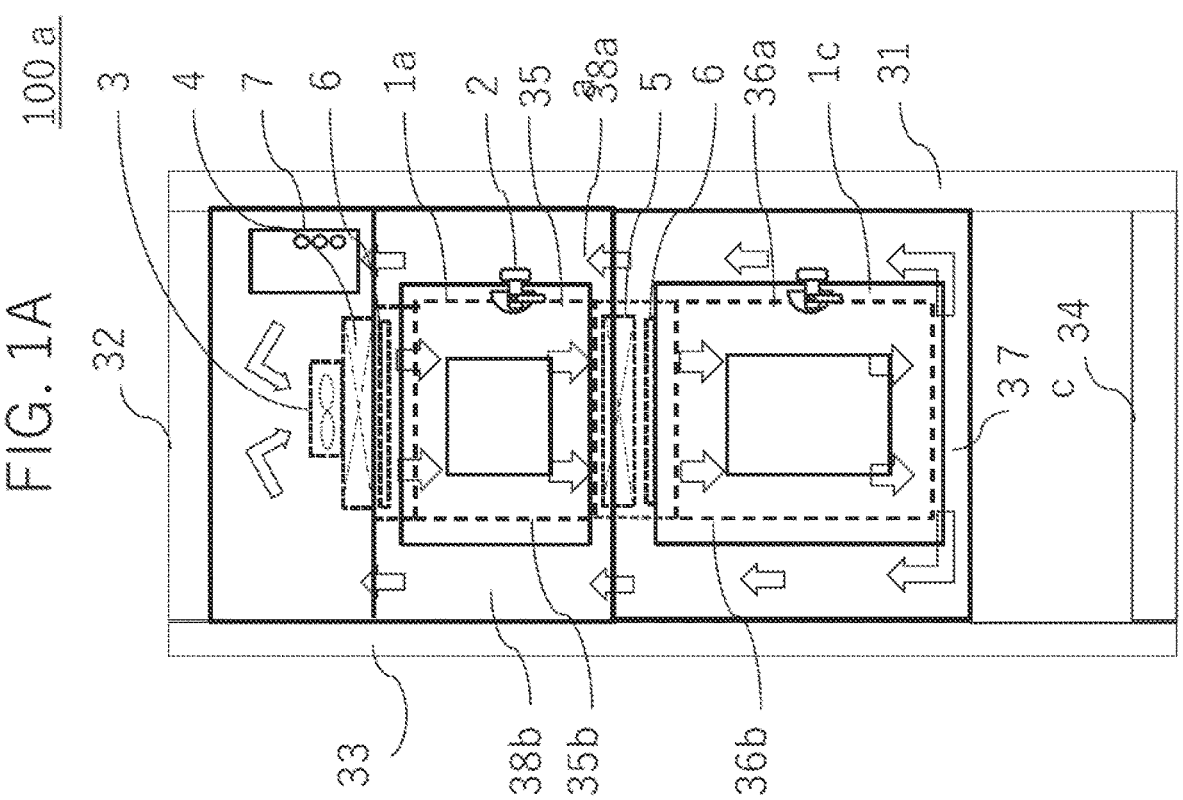
FIG. 1A is a front view illustrating an example of a two-stage (upper- and lower-stage) pass box of Example 1.

An embodiment of the present invention will be described with reference to the drawings. It should be noted that the same constituent elements in the drawings for describing the embodiment are given the same name and reference numeral as much as possible and repeated description thereof will be omitted.

The pass box according to the present embodiment is characterized in that a blower for air circulation is incorporated, the pass boxes are stacked in two (upper and lower) stages, and an airflow circulation path for returning the air that has passed through the two-stage (upper and lower) pass boxes to the blower again is provided so that the cleanliness in the pass box is maintained. In addition, a HEPA filter is disposed between the two-stage pass boxes. Here, HEPA filter stands for high efficiency particulate air filter.

Example 1

Figure 1B:
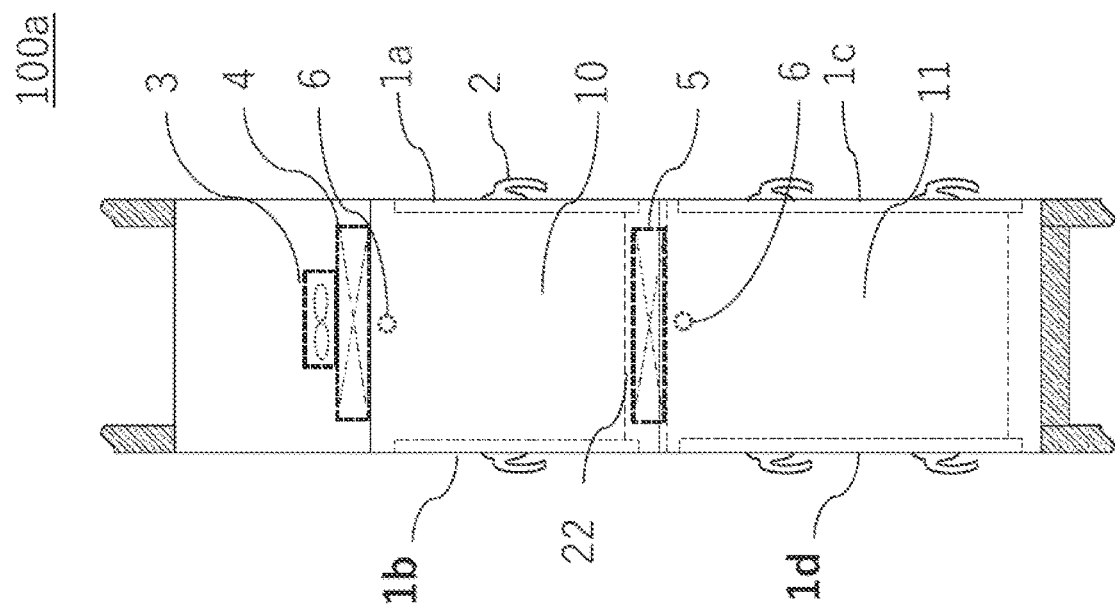
FIG. 1B is a right side view illustrating an example of the two-stage (upper- and lower-stage) pass box of Example 1.

FIGS. 1A and 1B are diagrams illustrating an example of the two-stage (upper and lower) pass boxes of Example 1, FIG. 1A is a front view, and FIG. 1B is a right side view.

A pass box 100a provides a space for delivering an article with respect to a clean room. As illustrated in FIG. 1B, the pass box 100a is separated into an upper space 10 and a lower space 11. The ceiling portion that is the upper portion of the upper space 10 is provided with an upper blower 3, an upper HEPA filter 4 provided downstream of the upper blower 3, and a germicidal lamp 6. The lower pass box is provided below the upper pass box. The ceiling portion that is the upper portion of the lower space 11 is provided with a lower HEPA filter 5 and the germicidal lamp 6.

The upper pass box of the pass box 100a has doors 1a and 1b in the front and rear, and the doors are opened and closed by a handle 2. For example, the door 1a is on the clean room side and the door 1b is on a contaminated area side. The upper space 10 is formed by the doors 1a and 1b, the upper HEPA filter 4, and an upper storage stand 22 (hereinafter, sometimes simply referred to as the storage stand) and provides a space for delivering an article with respect to the clean room. The side surface of the upper space 10 is configured by the doors 1a and 1b and the side wall of the upper space.

Meanwhile, the lower pass box has doors 1c and 1d in the front and rear and the doors are opened and closed by the handle. For example, the door 1c is on the clean room side and the door 1b is on the contaminated area side. The lower space 11 is formed by the doors 1c and 1d, the lower HEPA filter 5, and the storage stand and provides a space for delivering an article with respect to the clean room. The side surface of the lower space 11 is configured by the doors 1c and 1d and the side wall of the lower space.

As illustrated in FIG. 1A, the pass box 100a has side walls 31 and 33, a ceiling 32, and a floor 34. The side wall forms an airflow circulation path 38a between an upper space side wall 35a and a lower space side wall 36a. The side wall 33 forms an airflow circulation path 38b between an upper space side wall 35b and a lower space side wall 36b. The arrows in FIG. 1A indicate the airflow circulation path in the pass box 100a. A common airflow circulation path is configured, as indicated by the arrows, with respect to the two-stage (upper and lower) pass boxes by the pass boxes being stacked in two (upper and lower) stages and the airflow circulation path for returning the air that has passed through the two-stage (upper and lower) pass boxes to the blower again being provided as described above.

Air is sent by the upper blower 3, passes through the upper HEPA filter 4, becomes clean air, and passes through the upper space 10. The air that has passed through the upper space 10 passes through the lower HEPA filter 5, becomes clean air, and passes through the lower space 11. The lower HEPA filter 5 is provided between the lower ends of the door 1a and the door 1b and the upper ends of the door 1c and the door 1d. In a case where an article is in the upper space 10 and dust is generated from the article, clean air can be supplied to the lower space 11 by the lower HEPA filter 5 collecting the dust.

The air that has passed through the lower space 11 flows toward the side wall 31 and the side wall 33 through a lower path 37c and is taken into the upper blower 3 again via the airflow circulation paths 38a and 38b to form an airflow circulation path.

The pass box 100a has an electrical component unit 7 that controls a fan and displays the state of operation.

By means of the above-described configuration having the two-stage (upper and lower) pass boxes, it is possible to perform individual cleanliness maintenance even when the article delivery spaces are distinguished by the degree of importance or size of what is handled. For example, it is possible to prevent mutual contamination in the field of regenerative medicine where cells are cultured by using the upper space 10 for a sample such as cultured cells that are light and highly important and using the lower space 11 for cell culture equipment such as a pipette and a dish.

In addition, it is possible to simplify the configuration of the pass box and reduce the cost of the pass box by configuring the common airflow circulation path with respect to the two-stage (upper and lower) pass boxes.

Further, clean air is supplied to the upper space 10 and the lower space 11 by passing through the upper HEPA filter 4 and the lower HEPA filter 5, respectively.

FIGS. 2A and 2B illustrate comparative examples of the pass box installation. FIG. 2A illustrates a case where a pass box 101a is disposed above a pass box 101b. When the two independent pass boxes 101a and 101b are disposed such that the pass box 101a is disposed above the pass box 101b, a certain inter-pass box space 42 is necessary in addition to the thickness dimensions of the ceiling and the floor of each pass box. One of the reasons why the space 42 is necessary is that a wall is necessary for the floor of the pass box 101a and the ceiling of the pass box 101b to be supported. In addition, spaces 41a and 41b are necessary for each so that the blower and the HEPA filter are maintained.

Accordingly, the height of a pass box 101 increases. In addition, the height of the lower pass box 101b becomes close to the floor surface and the workability of opening and closing the pass box door deteriorates. Further, the risk of contamination increases as, for example, dust is rolled up from the floor surface due to the proximity to the floor surface.

FIG. 2B is a diagram illustrating a comparative example in which two pass boxes 101c and 101d are disposed side by side. When the independent pass boxes are disposed side by side, the occupancy of the breadth of the wall surface of the clean room increases although the height position can be suppressed, and thus it is necessary to secure a space near the pass box where the door needs to be opened and closed.

Accordingly, the interior of the clean room cannot be effectively used.

Example 2

FIG. 3 is an example in which a lower blower 26 is added to the pass box 100a of FIGS. 1A and 1B so that the air in the pass box does not leak out of the pass box even when a door 1 of the upper pass box is open. In Example 1, the upper space is pressurized by the upper blower 3 to have a positive pressure. Accordingly, in a case where the degree of sealing of the door 1 of the upper space 10 cannot be maintained, the dust generated in the upper space 10 may leak out to the clean room side by the air in the upper space 10 leaking out of the pass box from the gap of the door 1.

In a pass box 100b illustrated in FIG. 3, the internal pressure of the upper space 10 can be lowered or made negative by the lower blower 26. Accordingly, the possibility of air leaking out to the clean room side outside the pass box can be suppressed and the leakage of the dust in the pass box can be suppressed. Air leakage from the upper space 10 to the clean room can be suppressed if the lower blower 26 is continuously operated even with the door 1 of the upper space 10 open.

Figure 4:
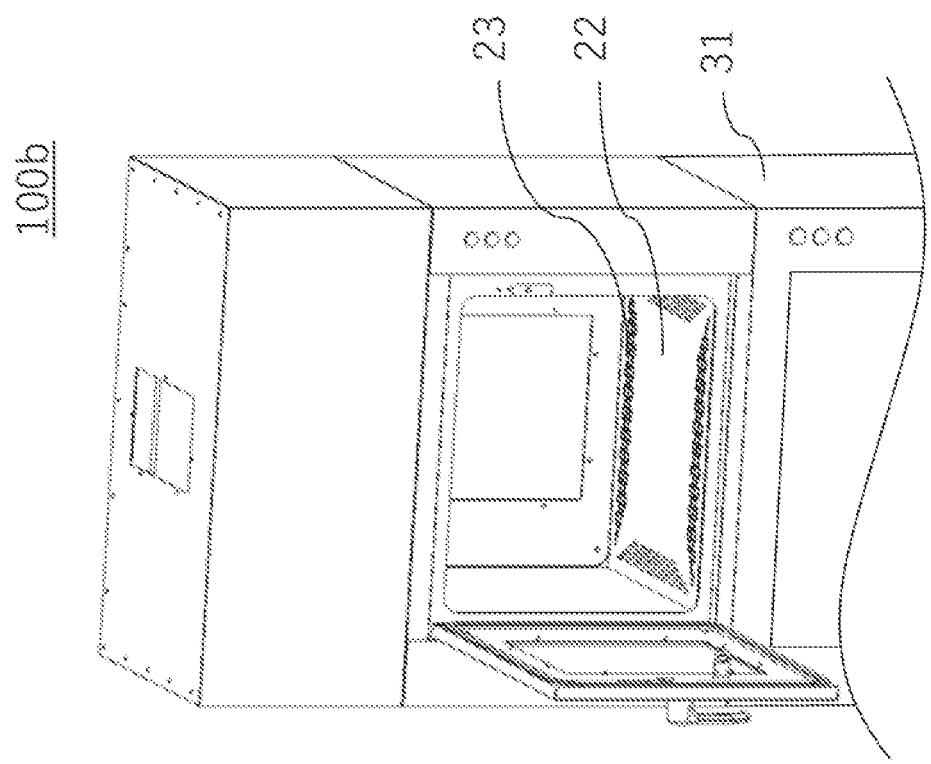
FIG. 4 is a diagram illustrating an example of a storage stand of Example 2.

FIG. 4 is a diagram illustrating the structure of the storage stand in the pass box 100b of FIG. 3 at a time when the door of the pass box 100b is open. In this example, a storage stand slit 23 allowing the passage of air is open in the peripheral portion of the storage stand 22. The middle flat portion of the storage stand 22, which is the middle of the storage stand where the storage stand slit 23 is not open, is used as a sample storage portion so that a sample is reliably protected from external contamination. In addition, air is suctioned by the lower blower 26 below the storage stand 22, and thus the sample storage portion in the middle of the storage stand 22 is isolated from the outside by an air barrier, external air does not flow into the sample storage portion even when the door is open, and the sample can be reliably protected from contamination.

A plurality of the storage stand slits 23 are provided in the vicinity of the door 1 around the storage stand 22. In addition, the storage stand slits 23 may be large in number near the door 1 and the number may decrease toward the middle portion of the storage stand 22.

It should be noted that the lower storage stand of the lower space 11 may have the same configuration as the upper storage stand 22.

Example 3

Figure 5:
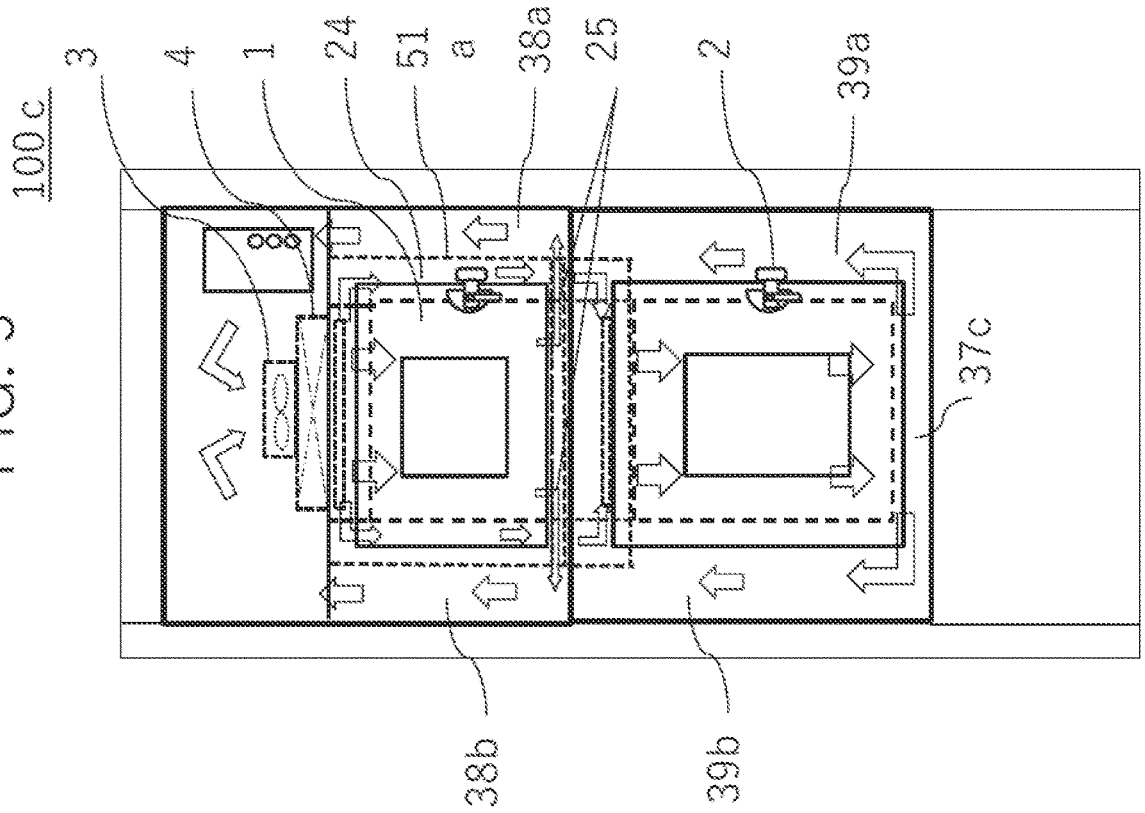
FIG. 5 is a diagram illustrating an example of a two-stage (upper- and lower-stage) pass box (without a lower HEPA filter) of Example 3.

FIG. 5 illustrates, as Example 3, an example of a structure in which the cleanliness of both the upper space 10 and the lower space 11 is maintained even without the lower HEPA filter 5 and the lower blower 26 in a pass box 100c, which has two (upper and lower) stages.

Two pass boxes are provided above and below as in the case of Example 1. Although the following description is repeated in part, the configuration of the pass box 100c will be described below with the reference numerals in FIGS. 1A and 1B used for elements common to Examples 1 and 3 so that the structure is comprehensible.

The pass box 100c is separated into the upper space 10 and the lower space 11. The ceiling portion that is the upper portion of the upper space 10 is provided with the upper blower 3, the upper HEPA filter 4 provided downstream of the upper blower 3, and the germicidal lamp 6. The lower pass box is provided below the upper pass box.

The upper pass box of the pass box 100c has the doors 1a and 1b in the front and rear, and the doors are opened and closed by the handle 2. For example, the door 1a is on the clean room side and the door 1b is on the contaminated area side. The upper space 10 is formed by the doors 1a and 1b, the upper HEPA filter 4, and the storage stand 22 and provides a space for delivering an article with respect to the clean room. The side surface of the upper space 10 is configured by the doors 1a and 1b and the side wall of the upper space.

Meanwhile, the lower pass box has the doors 1c and 1d in the front and rear and the doors are opened and closed by the handle. For example, the door 1c is on the clean room side and the door 1d is on the contaminated area side. The lower space 11 is formed by the doors 1c and 1d, the lower HEPA filter 5, and the storage stand and provides a space for delivering an article with respect to the clean room. The side surface of the lower space 11 is configured by the doors 1c and 1d and the side wall of the lower space.

The pass box 100c has the side walls 31 and 33, the ceiling 32, and the floor 34. The side wall 31 forms the airflow circulation path 38a and an airflow circulation path 39a between the upper space side wall 35a and the lower space side wall 36a. The side wall 33 forms the airflow circulation path 38b and an airflow circulation path 39b between the upper space side wall 35b and the lower space side wall 36b. The arrows in FIG. 5 indicate the airflow circulation path in the pass box 100c. It should be noted that the airflow circulation paths 38a and 39a and the airflow circulation paths 38b and 39b constitute a common airflow circulation path with respect to the two-stage (upper and lower) pass boxes as indicated by the arrows and as in the case of Example 1.

Air is pushed in by the upper blower 3, passes through the upper HEPA filter 4, becomes clean air, and passes through the upper space 10. The clean air that has passed through the upper space 10 passes through an upper exhaust path 25 without passing through the lower space 11 and returns to the upper blower 3. The upper exhaust path 25, which is provided between the upper space 10 and the lower space 11, is for sending the air that has passed through the upper space 10 toward the side walls 31 and 33 of the upper pass box and returning the air to the upper blower 3 by merging with the airflow circulation path 38a and the airflow circulation path 38b. The upper exhaust path 25 has a shape in which one end of the upper exhaust path 25 covers the storage stand slit 23 provided in the storage stand 22 and the other end merges with the airflow circulation path 38a and the airflow circulation path 38b. The shape of the upper exhaust path 25 is not particularly limited insofar as the air taken in from the storage stand slit 23 can be sent to the airflow circulation path 38a and the airflow circulation path 38b and returned to the upper blower 3. For example, the upper exhaust path 25 may be configured to perform suction from the storage stand slit 23 in the form of two (left and right) tubes and discharge to the airflow circulation path 38a and the airflow circulation path 38b.

Meanwhile, the clean air supply with respect to the lower space 11 bypasses the upper space 10 by passing through an upper bypass path 24 after cleaning through the upper HEPA filter 4. The upper bypass path 24 is provided between the upper space side wall 35a and the side wall 31 and between the upper space side wall 35b and the side wall 33 and is separated from an airflow circulation path 38. For example, the upper bypass path 24 has a tubular or plate-shaped separation wall that separates the upper bypass path 24 from the airflow circulation path 38.

The air that has passed through the lower space 11 returns to the upper blower 3 via the lower path 37c and an airflow circulation path 39. The airflow circulation path 39 is provided between the side walls 31 and 33 of the pass box and the lower space side wall that forms the lower space 11 and is capable of returning the air that has flowed from below the lower space 11 toward the side wall 31 and the side wall 33 via the lower path 37c to the upper blower 3 again via the airflow circulation paths 38a and 38b.

In this manner, the common airflow circulation paths 38a, 39a, 38b, and 39b are configured with respect to the two-stage (upper and lower) pass boxes as in the case of Example 1.

As a result, the cleanliness of the two-stage pass boxes can be maintained by means of one HEPA filter and cost reduction is achieved.

As described above, according to each example, it is possible to prevent inter-article mutual contamination by delivering different articles in isolated spaces.

In addition, it is possible to ensure the cleanliness of each article delivery space.

In addition, the height of the pass box can be suppressed by the storage spaces being disposed in two (upper and lower) stages and it is possible to provide a pass box with improved workability for putting in and taking out articles.

REFERENCE SIGNS LIST

1 Door
2 Handle
3 Upper blower
4 Upper HEPA filter
5 Lower HEPA filter
6 Germicidal lamp
7 Electrical component unit
10 Upper space
11 Lower space
22 Storage stand
23 Storage stand slit
24 Upper bypass path
25 Upper exhaust path
26 Lower blower
31 Side wall
33 Side wall
35 Upper space side wall
36 Lower space side wall
37 Lower path
38 Airflow circulation path
39 Airflow circulation path

The invention claimed is:

1. A pass box delivering an article with respect to a clean room, the pass box comprising an upper pass box and a lower pass box, wherein
the upper pass box includes:
an upper blower provided in an upper portion;
an upper HEPA filter provided downstream of the upper blower;
a first door provided on the clean room side;
a second door provided on a contaminated area side on a side opposite to the clean room; and
an upper storage stand forming an upper space performing article delivery together with the first door, the second door, and the upper HEPA filter,
the lower pass box is provided below the upper pass box and includes:
a lower HEPA filter provided downstream of the upper space;
a third door provided on the clean room side;
a fourth door provided on the contaminated area side on the side opposite to the clean room; and
a lower storage stand forming a lower space performing article delivery together with the third door, the fourth door, and the lower HEPA filter, and
the pass box has an airflow circulation path returning air to the upper blower after the air is passed through the upper space and the lower space by the upper blower.

2. The pass box according to claim 1,
wherein the airflow circulation path is formed between an upper space side wall forming the upper space and a side wall of the pass box, is formed between a lower space side wall forming the lower space and the side wall of the pass box, and returns air to the upper blower after the air passes through the lower space.

3. The pass box according to claim 2,
wherein the lower HEPA filter is provided between lower ends of the first door and the second door and upper ends of the third door and the fourth door.

4. The pass box according to claim 3, further comprising a lower blower between the upper space and the lower space and above the lower HEPA filter.

5. The pass box according to claim 2,
wherein the upper storage stand has air passage slits in a peripheral portion.

6. The pass box according to claim 5,
wherein the number of the slits is larger on the peripheral portion side than on a central portion side of the upper storage stand.

7. A pass box delivering an article with respect to a clean room, the pass box comprising an upper pass box and a lower pass box, wherein
the upper pass box includes:
an upper blower provided in an upper portion;
an upper HEPA filter provided downstream of the upper blower;
a first door provided on the clean room side;
a second door provided on a contaminated area side on a side opposite to the clean room; and
an upper storage stand forming an upper space performing article delivery together with the first door, the second door, and the upper HEPA filter,
the lower pass box is provided below the upper pass box and includes:
a third door provided on the clean room side;
a fourth door provided on the contaminated area side on the side opposite to the clean room; and
a lower storage stand forming a lower space performing article delivery together with the third door and the fourth door,
an upper exhaust path allows air to flow toward a side wall of the upper pass box after the air passes through the upper space,
a first airflow circulation path is formed between the side wall of the upper pass box and an upper space side wall forming the upper space to return air to the upper blower after the air passes through the upper space and the upper exhaust path from the upper blower, and an upper bypass path bypassing the upper space from the upper blower and sending air into the lower space and a second airflow circulation path returning the air to the upper blower between a side wall of the pass box and a lower space side wall forming the lower space are formed.

8. The pass box according to claim 7, wherein the upper bypass path is provided between the side wall of the upper pass box and the upper space side wall forming the upper space and has a separation wall for separation from the first airflow circulation path.

\* \* \* \* \*